US006596520B1

(12) United States Patent
Friedrich et al.

(10) Patent No.: US 6,596,520 B1
(45) Date of Patent: Jul. 22, 2003

(54) IMMOBILIZING LIPASE BY ADSORPTION FROM A CRUDE SOLUTION ONTO NONPOLAR POLYOLEFIN PARTICLES

(75) Inventors: Thomas Friedrich, Darmstadt (DE); Rainer Stürmer, Rödersheim-Gronau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 30 days.

(21) Appl. No.: 09/610,943

(22) Filed: Jul. 6, 2000

(30) Foreign Application Priority Data

Jul. 9, 1999 (DE) .......................... 199 31 847

(51) Int. Cl.⁷ ............................. C12P 7/62; C12P 13/00; C12P 41/00; C12M 11/08; C12M 9/20
(52) U.S. Cl. ..................... 435/135; 435/128; 435/132; 435/134; 435/136; 435/155; 435/180; 435/198; 435/280; 435/874; 435/875
(58) Field of Search ................... 435/134, 135, 435/177, 180, 280, 874, 875, 128, 132, 136, 155, 198

(56) References Cited

U.S. PATENT DOCUMENTS

| 4,818,695 A | * | 4/1989 | Eigtved | 435/134 |
|---|---|---|---|---|
| 5,021,345 A | * | 6/1991 | Urban et al. | 435/180 |
| 5,102,799 A | | 4/1992 | Urban et al. | 435/180 |
| 5,108,916 A | * | 4/1992 | Cobbs et al. | 435/135 |
| 5,387,514 A | | 2/1995 | Schudok et al. | 435/135 |
| 5,523,233 A | * | 6/1996 | Chartrain et al. | 435/280 |
| 5,770,438 A | * | 6/1998 | Nakahama et al. | 435/280 |
| 5,962,285 A | * | 10/1999 | Anderson et al. | 435/142 |
| 6,234,811 B1 | * | 5/2001 | Balkenhohl et al. | 435/119 |

FOREIGN PATENT DOCUMENTS

| EP | 232 933 | 8/1987 |
|---|---|---|
| EP | 0 345 658 | 12/1989 |
| EP | 0 492 497 | 7/1992 |
| EP | 0 655 504 | 5/1995 |
| WO | WO 90/15868 | 12/1990 |
| WO | WO 94/28118 | 12/1994 |
| WO | WO 95/17504 | 6/1995 |

* cited by examiner

*Primary Examiner*—David M. Naff
(74) *Attorney, Agent, or Firm*—Keil & Weinkauf

(57) ABSTRACT

Immobilized lipase is prepared by adsorbing lipase from a crude lipase solution onto polyolefin particles such as polypropylene particles which are nonpolar. The crude solution may be a cell-free culture broth. Lipase sources include *Pseudomonas burkholderia* and *Pseudomonas aeruginosa*. Uses of the immobilized lipase include enantioselective conversion of substrates such as enantioselective acylating or hydrolyzing.

10 Claims, No Drawings

IMMOBILIZING LIPASE BY ADSORPTION FROM A CRUDE SOLUTION ONTO NONPOLAR POLYOLEFIN PARTICLES

FIELD OF INVENTION

The present invention relates to a process for preparing immobilized lipase, to the immobilized lipase itself and to a process for enzyme-catalyzed conversion in the presence of the immobilized lipase.

BACKGROUND OF THE INVENTION

Lipases can be used in solution as enzymatic catalysts for converting substrates. Immobilized lipases are distinguished from free lipases by having an increased stability and useful life on carrying out the reaction continuously and batchwise, and by easy recovery of the catalytically active species in batchwise reactions.

It is known to immobilize lipases by adsorption onto a solid support. It is also known to prepare immobilized lipases by contacting polyolefin particles with an aqueous solution of a purified lipase.

EP 232 933 describes the immobilization of a purified lipase from an aqueous solution by adsorption onto hydrophobic thermoplastic polymers such as, for example, aliphatic polyolefins. The immobilized lipase is used for fat hydrolysis.

WO 90/15868 discloses the immobilization of purified *Candida antarctica* lipase from an aqueous solution by adsorption onto aliphatic polyolefins which have been pretreated with organic solvents. The immobilized lipase is used for ester synthesis.

In WO 94/28118 a nonionic surface-active substance is added before immobilization of the purified lipase on hydrophobic support materials.

All prior art processes have the disadvantage that the lipase is purified to remove other proteins, enzymes and other cell constituents from the crude lipase solution before the immobilization on the solid support. This purification step by precipitation and chromatographic processes is time-consuming and costly.

In addition, the immobilized lipases prepared according to the prior art have a greatly reduced activity compared with the free lipases and must be reactivated by adding, for example, surface-active substances.

Addition of surface-active substances is also necessary to activate free lipases in organic solution which have been purified from a crude lipase solution according to the prior art (WO 95/17504).

In addition, the useful life of the immobilized lipases prepared according to the prior art is still not optimal.

SUMMARY OF THE INVENTION

It is an object of the present invention to remedy the described deficiencies and provide a novel simplified process for preparing immobilized lipase and novel immobilized lipases which have optimized properties and have been prepared by a simplified process.

We have found that these objects are achieved by a novel process for preparing immobilized lipase, in which a crude lipase solution is contacted with polyolefin particle.

DETAILED DESCRIPTION OF THE INVENTION

A crude lipase solution means, for example, a lipase solution which contains more than 2% by weight, preferably more than 5% by weight, particularly preferably more than 15% by weight, of impurities such as, for example, other proteins, other cellular constituents of the lipase-producing organism or residues of nutrient media. The lipase can be present in aqueous solution or else in aqueous buffer systems or in organic solvents such as, for example, in optionally halogenated aliphatic or aromatic hydrocarbons such as, for example, toluene. An aqueous crude lipase solution is preferred.

Preferred aqueous crude lipase solutions are, for example, culture broths obtained by cultivation of a lipase-producing organism in an aqueous nutrient medium, or obtainable by dispersing and/or homogenizing a lipase-producing organism or a lipase-producing cellular tissue, such as, for example, of an animal organ or of a plant, in an aqueous solvent containing, where appropriate, a buffer or other lipase-stabilizing ingredients.

The crude lipase solution is preferably purified, before contacting with the polyolefin particles, to remove cells by methods known per se, such as centrifugation or filtration.

The contacting takes place, for example, by introducing the polyolefin particles into the crude lipase solution.

When the crude lipase solution is contacted with the polyolefin particles, the lipase is adsorbed onto the polyolefin particles. It was surprising in this connection that polyolefin particles have a very high selectivity for lipases so that there is adsorption from the crude lipase solution onto the polyolefin only of the lipase and, where appropriate, its fragments and not—or only to a very small extent (usually <2% by weight)—the other proteins.

The adsorption step is thus also a step to purify the lipase from the other proteins and enzymes in the crude lipase solution, so that another purification step before the immobilization on the solid support can be omitted for the crude lipase solution. Besides simplified preparation, the immobilized lipases prepared in this way have the following advantages over prior art immobilized lipases:

The immobilized lipase has a longer useful life.
The addition of activated substances such as, for example, oleic acid is no longer necessary and brings about no increase in activity.

It is possible in principle also to use further purified crude lipase solutions for the process according to the invention. The crude lipase solution can be purified, for example, up to the point where addition of oleic acid to the immobilized lipase again brings about a jump in activity.

Suitable purification steps are all conventional processes for protein purification such as, for example, ion exchange chromatography, molecular sieve chromatography, hydrophobic chromatography and precipitation methods.

However, it is preferred to use an unpurified, cell-free crude lipase solution in the process according to the invention.

Accordingly, a preferred process for preparing immobilized lipase is one in which the crude lipase solution is a cell-free culture broth which is obtainable by a) cultivating a lipase-producing organism,
b) where appropriate subsequently dispersing and/or homogenizing the organism in a solution and
c) subsequently removing the cells.

A lipase-producing organism means an organism which is able by nature or through genetic modification, for example by insertion of a lipase gene into the genome of the organism, to produce a lipase. Organism means microorganisms, plants and animals, as well as cellular tissue of animal or plant origin.

Preferred bacterial and fungal lipases are derived from organisms of the genus Aspergillus, Arthrobacter, Alcaligenes, Bacillus, Brevibacterium, Pseudomonas, Chromobacterium, Candida, Fusarium, Geotrichum, Humicola, Mucor, Pichia, Penicillium, Rhizomucor, Rhizopus or Thermus.

Particularly preferred bacterial and fungal lipases are lipases from the genera and species Arthrobacter sp., Alcaligenes sp., *Aspergillus niger, Aspergillus oryzae, Bacillus cereus, Bacillus subtilis, Bacillus coagulans, Brevibacterium ammoniagenes, Burkholderia plantarii, Candida antarctica, Candida cylindracea, Candida lipolytica, Candida utilis, Candida rugosa, Chromobacterium viscosum, Fusarium solani, Geotrichum candidum, Humicola lanuginosa,* Mucor sp., *Mucor japonicus, Mucor javanicum, Mucor miehei, Pichia miso, Rhizopus nigricans, Rhizopus oryzae, Rhizopus arrhizus,* Rhizopus sp., *Rhizomucor miehei, Rhizopus arrhizus, Rhizopus delemar, Rhizopus niveus, Penicillium acylase, Penicillium roqueforti, Thermus aquaticus, Thermus flavus, Thermus thermophilus, Chromobacterium viscosum,* Pseudomonas sp., *Pseudomonas putida, Pseudomonas fluorescens, Pseudomonas cepacia, Pseudomonas burkholderia* or *Pseudomonas aeruginosa.*

Preferred animal and plant lipases are pig pancreatic lipase (PPL) and wheatgerm lipase.

Particular preference is given to the lipase from *Pseudomonas burkholderia* (former name: *Burkholderia plantarii*) or *Pseudomonas aeruginosa*, and the use of *Pseudomonas burkholderia* or *Pseudomonas aeruginosa* as lipase-producing organism.

The cultivation of microorganisms or plant or animal cell cultures can take place in a manner known per se, for example by fermentation in a nutrient medium which, besides nutrients, trace elements and, where appropriate, antibiotics, contains, for example, a buffer system to stabilize the proteins and enzymes. It is usually possible in this case to omit step b), the dispersion and/or homogenization.

Plants, animals and cellular tissue of animal or plant origin, such as organs or parts of plants, can be cultivated in a manner known per se, for example in nutrient media or in animals, and be harvested or isolated in a manner known per se. The culture broth is then preferably prepared in a manner known per se by dispersing and/or homogenizing the plants or cellular tissue in a solvent, preferably in water or an aqueous buffer solution and subsequently removing the cells.

Polyolefin particles mean particles of polyolefins. Preferred polyolefins are homopolymers or copolymers of optionally substituted olefins such as, for example, ethylene, propylene, butadiene, butene or octene. Particularly preferred polyolefin particles are particles of polypropylene such as, for example, polypropylene particles obtainable under the name ACCUREL® (from Akzo via Enka AG, Obernburg, Germany).

The size and the void fraction of the polyolefin particles is not critical. Preferred particles have, because they are easier to handle, a size of from 100 µm to 2000 µm, and particularly preferred particles have a size of from 200 µm to 1000 µm. The void fraction of the polyolefin particles is advantageously 40%–80%, particularly preferably 60%–70%, very particularly preferably 65%.

The pore size of the polyolefin particles is preferably 0.01 µm to 1 µm, particularly preferably 0.05 µm to 0.5 µm, The lipase loading of the polyolefin particles is not critical. The preferred loading at which the maximum amount of lipase is adsorbed and not too much lipase is lost in excess depends on the nature of the polymer and can be found by routine tests. In the preferred use of polypropylene particles, a loading of 2 mg–6 mg of lipase per g of polyolefin particles is preferred, and a loading of 4.2 mg of lipase is particularly preferred.

The influence of the pH of the crude lipase solution on the degree of loading is not critical. High degrees of loading are achieved at a pH between 4 and 7. A pH between 4.5 and 5.5 is preferred, and a pH of 4.8 is particularly preferred.

The influence of the ionic strength of the crude lipase solution on the degree of loading is likewise not critical. High degrees of loading are achieved with an ionic strength of less than 500 mM. An ionic strength of less than 300 mM is particularly preferred.

The optimal duration of the loading process depends on the lipase and the nature of the polyolefin particles and can be determined by routine tests. The final degree of-loading is usually reached after a contact time between the polyolefin particles and the crude lipase solution of 4 to 6 hours.

The immobilized lipases prepared by this process can be employed directly in the enzymatic reactions described hereinafter. Activation, for example by addition of oleic acid, is unnecessary.

It is advantageous for the immobilized lipase to be purified, before use in a reaction, to remove unadsorbed material, for example by washing with a suitable solvent, such as, for example, water. The immobilized lipase can then, where appropriate, be dried by methods known per se, such as, for example, by drying in the air.

The invention further relates to an immobilized lipase obtainable by the preparation process described above.

The invention further relates to a process for the enzyme-catalyzed conversion or enantioselective conversion of substrates by reacting the substrates in the presence of the immobilized lipase according to the invention.

The immobilized lipase according to the invention is accordingly used as catalyst.

Enzyme-catalyzed conversions mean chemical reactions of substrates which the lipases are able to catalyze in the nonimmobilized, free state in solution. The following reactions may be mentioned as examples:

acylation or enantioselective acylation of alcohols, acylation or enantioselective acylation of amines, acylation or enantioselective acylation of amino esters such as, for example, esters of amino acids, hydrolysis or enantioselective hydrolysis of carboxylic esters, acylation or enantioselective acylation of cyanohydrins, hydrolysis or enantioselective hydrolysis of cyanohydrin esters, asymmetrization of meso diols or asymmetrization of meso diesters by hydrolysis.

Preferred processes are processes for acylation or enantioselective acylation of alcohols, acylation or enantioselective acylation of amines, acylation or enantioselective acylation of amino esters such as, for example, esters of amino acids or a process for the hydrolysis or enantioselective hydrolysis of carboxylic esters.

The immobilized lipase particularly preferably used in these processes is one from *Pseudomonas burkholderia* (former name: *Burkholderia plantarii*) or *Pseudomonas aeruginosa*, which has been prepared by the preparation process according to the invention described above.

The process for the enzyme-catalyzed conversion or enantioselective conversion of substrates comprises reacting the substrates in the presence of the immobilized lipase.

It is preferred for further reagents to be added if the reaction type requires this. Thus, for example, an acylation requires addition of an acylating agent, whereas, for example, hydrolysis requires no addition of other reagents.

A substrate means a chemical compound which can be reacted, i.e. chemically altered, with enzyme catalysis by lipases. In enantioselective conversions, mixtures of stereoisomers of which only one is reacted are likewise substrates.

Examples of substrates which may be mentioned are alcohols, amines, amino esters, amides, carboxylic esters, thioesters, thiols, cyanohydrins, cyanohydrin esters and meso diols and mixtures of stereoisomers thereof. Preferred substrates are alcohols, amines, amino esters and carboxylic esters, and racemic alcohols, amines, amino esters and carboxylic esters.

The process is preferably carried out in solution, with or without solvent in the case of liquid substrates. Examples of solvents which can be used are water, organic solvents or else aqueous/organic two-phase mixtures.

The organic solvents preferably used are dioxane, THF, diethyl ether, methyl t-butyl ether (MTBE), toluene or heptane. The aqueous/organic two-phase mixture preferably employed is a water/MTBE mixture in any suitable ratio.

When the process is carried out in solution, the substrate concentration is not critical but is preferably between 0.5% by weight and 50% by weight based on the solution, particularly preferably 20 to 30% by weight. The temperature for carrying out the process is likewise not critical but the upper limit is determined by the thermal stability of the lipase in the polymer.

The process is preferably carried out at from 0° C. to 60° C., particularly preferably 15° C. to 40° C.

The process can be carried out continuously or batchwise. To carry out the process continuously, for example, a liquid mobile phase is passed in a manner known per se through a bed of immobilized lipase in a reactor. The mobile phase can be either a solution of substrate (and reagents) or the liquid substrates (and reagents) without solvent. The flow rate is not critical and depends on technical aspects of the process, such as the height, diameter and particle size of the bed, and on the design of the reactor.

The reactors preferably used for the continuous process are the reactors customary for continuous heterogeneously catalyzed processes (liquid/solid reactions) (J. Hagen, Chemische Reaktionstechnik, VCH, Weinheim 1992, pp. 165–169). Examples which may be mentioned are fluidized bed reactors and fixed bed reactors, such as tubular reactor, column reactor, full space reactor, quench tube reactor, tube bundle reactor and flat bed contact reactor.

When the process is carried out batchwise, the immobilized lipases are suspended in a manner known per se in a solution of substrate (and reagents) or in liquid substrates (and reagents), with or without solvent, in a reactor, and the suspension is mixed. The reactors preferably used for the batchwise process are the reactors customary for batchwise heterogeneously catalyzed processes (liquid/solid reactions) with shaking, mixing or stirring device. Examples which may be mentioned are a stirred vessel and designs generated therefrom, and reaction vessels with shaking device.

After the reaction is complete (thermodynamic equilibrium reached), the immobilized lipase is isolated, for example by decantation, centrifugation or filtration and washing, and used in further reactions.

In a preferred embodiment of the process, substrates which contain functional groups which can be acylated, such as, for example, hydroxyl or amino groups, such as alcohols, amines or amino esters, are acylated or enantioselectively acylated in the presence of the immobilized lipase as catalyst and of an acylating agent.

This enzyme-catalyzed conversion is preferably carried out in an organic solvent such as, for example, dioxane, THF, diethyl ether, methyl t-butyl ether (MTBE), toluene or heptane.

A particularly preferred process is one for the acylation or enantioselective acylation of alcohols, amines or amino esters or racemic alcohols, amines or amino esters in the presence of an acylating agent and of an immobilized lipase from *Pseudomonas burkholderia* or *Pseudomonas aeruginosa*.

There is virtually no restriction on the alcohols, amines and amino esters. Thus, it is possible to use monohydric and polyhydric alcohols such as, for example, 1-phenylethanol, 2-chloro-1-phenylethanol, 2-chloro-1-(m-chlorophenyl)ethanol, pent-3-yn-2-ol, 1-butyn-3-ol, 2-hydroxy-4-phenylbutyric esters, a-methyl-(1,3)-benzodioxole-5-ethanol, 1-(1,3-benzodioxol-4-yl)-2-propanol, trans-2-methoxycyclohexanol or 2-methoxy-2-phenylethanol or mixtures of stereoisomers thereof, monofunctional and polyfunctional amines or their stereoisomeric mixtures or α,β or γ-amino esters such as, for example, the optionally halogen-substituted $C_1$–$C_4$-alkyl, alkylaryl, aryl, $C_2$–$C_6$-alkenyl or $C_2$–$C_6$-alkynyl esters of the natural amino acids or mixtures of stereoisomers thereof.

Acylating agents mean organic compounds able to act as acyl donors in the presence of lipases in solution. Examples which may be mentioned are:

aliphatic, araliphatic or aromatic carboxylic acids optionally substituted by halogen such as Cl, Br, I, F (acylation), such as $C_1$–$C_6$-alkanecarboxylic acids, for example formic acid, acetic acid, propionic acid, butyric acid or such as araliphatic or aromatic carboxylic acids, for example benzoic acid, 3-phenylpropionic acid or the corresponding carboxylic esters (transesterification) such as, for example, 3-phenylpropionic esters or alkyl acetates such as, for example, ethyl acetate.

Carboxylic esters preferred as acylating agents are vinyl esters of the formula I

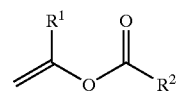

in which $R^1$ is hydrogen or a $C_1$–$C_4$-alkyl, preferably methyl, group and $R^2$ is hydrogen, $C_1$–$C_{18}$-alkyl which is optionally halogen-substituted, phenyl or $(C_1$–$C_3)$-alkoxy-$(C_1$–$C_4)$-alkyl, such as vinyl formate, vinyl acetate, vinyl propionate, vinyl butyrate or vinyl laurate.

Further acylating agents are aliphatic, cycloaliphatic, araliphatic or aromatic carboxylic anhydrides and mixed carboxylic anhydrides (acylation) such as acetic anhydride, succinic anhydride, butyric anhydride, 2-ethylhexanoic anhydride or methylsuccinic anhydride. When succinic anhydride or other anhydrides of low solubility are used as acylating agents it is possible particularly advantageously to admix propylene carbonate in order to dissolve the succinic anhydride. This is particularly important in relation to a continuous process.

In another preferred embodiment of the process, carboxylic esters are hydrolyzed or enantioselectively hydrolyzed in the presence of the immobilized lipase.

In this case there is no need to add any other reagents, although the presence of water is necessary. The hydrolysis of carboxylic esters is preferably carried out by adding water with use of a preferably two-phase system such as, for example, water/MTBE in the presence of the immobilized lipase.

A particularly preferred process for the hydrolysis or enantioselective hydrolysis of carboxylic esters takes place in the presence of an immobilized lipase according to the invention from *Pseudomonas burkholderia* or *Pseudomonas aeruginosa*.

There is virtually no restriction on the carboxylic esters. Thus, for example, it is possible to use compounds of the formula II or mixtures of stereoisomers thereof

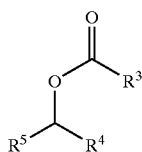

II where $R^3$, $R^4$ and $R^5$ are, independently of one another, hydrogen, halogen such as, for example, F, Cl, Br or I, a branched or unbranched, optionally substituted $C_1$–$C_8$-alkyl radical, such as, for example, optionally substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, heptyl or octyl, $C_2$–$C_6$-alkenyl radical such as, for example, optionally substituted 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, $C_3$–$C_6$-alkynyl radical such as, for example, optionally substituted 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl or $C_3$–$C_8$-cycloalkyl radical such as, for example, optionally substituted cyclopropyl, cyclobutyl, cyclopentyl, cyclohexyl, cycloheptyl and cyclooctyl, an optionally substituted aryl radical such as, for example, optionally substituted phenyl, 1-naphthyl or 2-naphthyl, arylalkyl radical such as, for example, optionally substituted benzyl, hetaryl radical, such as, for example, optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl or 6-pyridazinyl, preferably 2-pyridyl, 3-pyridyl, 4-pyridyl, 2-furyl, 3-furyl, 2-thienyl, 3-thienyl, 2-thiazolyl, 4-thiazolyl or 5-thiazolyl, or heterocycloalkyl or -alkenyl radical.

Suitable single or triple substituents of the $C_1$–$C_8$-alkyl, $C_2$–$C_6$-alkenyl, $C_2$–$C_6$-alkynyl, $C_3$–$C_8$-cycloalkyl, aryl, arylalkyl, hetaryl, heterocycloalkyl or -alkenyl radicals are, for example, halogen, nitro, amino, hydroxyl or cyano groups, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, hetaryl, aryl radicals or the —O—CO—$C_f$–$C_4$-alkyl radical.

Examples of preferred carboxylic esters are 1-butyn-3-yl acetate, 1-butyn-3-yl butyrate, 1-phenylethyl acetate or 2-acetoxy-4-phenylbutyric esters.

The process for the enantioselective enzyme-catalyzed conversion of substrates using the immobilized lipases according to the invention can be used for removing stereoisomers and, in particular, for removing enantiomers or diastereomers from a mixture of stereoisomers of the substrate. It is particularly preferably used for removing enantiomers or diastereomers from racemic substrates and thus for preparing optically active compounds from the respective racemic mixtures.

The enantioselective substrate specificity of the immobilized lipase means, for example, that only one enantiomer of the racemic substrate is converted, and the other enantiomer does not react. The resulting products can be easily separated in a manner known per se by chemical, physical and mechanical separation methods. Examples which may be mentioned are crystallization, precipitation, extraction in two-phase solvent systems, chromatographic separation methods such as HPLC, GC or column chromatography on silica gel or thermal separation methods such as distillation.

Accordingly, the present invention further relates to a process for preparing optically active compounds, which comprises mixtures of stereoisomers or racemates of substrates which can be reacted with enzyme catalysis by lipases being reacted enantioselectively in the presence of the immobilized lipase according to the invention, and then the mixtures being fractionated.

The process according to the invention can be used preferably to prepare the optically active compounds which can as mixtures of stereoisomers be reacted as substrates of lipases, or of whose mixture of stereoisomers at least one stereoisomer can be reacted as substrate of lipases.

A process for the enantioselective acylation of alcohols, amines or amino esters is preferably used for resolving racemic alcohols, amines or amino esters and thus for preparing optically active alcohols, amines or amino esters.

A process for the enantioselective hydrolysis or hydrolysis of carboxylic esters is preferably used for resolving racemic carboxylic esters and thus for preparing optically active carboxylic esters.

The following examples illustrate the invention:

EXAMPLE 1

Preparation of Immobilized Lipases 1.1 Cultivation of a lipase-producing organism taking the example of *Pseudomonas burkholderia* fermentation The strain *Pseudomonas burkholderia* was employed in a 14 l fermentation. The preculture contained:

| | |
|---|---|
| 1 | g/l $MgSO_4 * 7 H_2O$ |
| 3.5 | g/l $KH_2PO_4$ |
| 3.5 | g/l $K_2HPO_4$ |
| 5.0 | g/l $(NH_4)H_2PO_4$ |
| 0.02 | g/l $CaCl_2 * 2 H_2O$ |
| 10 | g/l yeast extract (Difco) |

In each case 200 ml of medium were sterilized in a 1 l shaken flask with 2 base baffles tat 121° C. for 30 mi, and 1 ml of trace elements (2-fold concentrated) was added to each flask. For a 14 l fermenter, 2 shaken flasks were incubated with *Pseudomonas burkholderia* at 30° C. and 200 rpm for 7–9 hours.

Fermenter configuration: Standard-configuration Techfors fermenter with a pH electrode (acid and alkali control), $pO_2$ electrode and antifoam electrode (Russell).

Peripherals:

2 l glass bottle with Masterflex tubing and a connecting needle was filled with about 2 kg of soybean oil and sterilized at 121° C. for 30 mn.

2 empty 1 l glass bottles (for metering acid and alkali) with connecting needles we re sterilized at 121° C. for 30 min. The sterilized bottles were the n charged with 500 ml of aqueous ammonia (25%) and 500 ml of sulfuric acid (20%).

1 glass bottle filled with Tegosipon 3062 (about 500 ml) with connecting needle was sterilized at 121° C. for 30 min.

Sartorius metering line with weigher and Watson-Marlow pump for oil metering for the addition of soybean oil.

The mixture for the fermentation medium consisted of:

| | |
|---|---|
| 110 | g of yeast extract (Difco) |
| 38.5 | g of $K_2HPO_4$ |
| 38.5 | g of $KH_2PO_4$ |
| 55 | g of $(NH_4)H_2PO_4$ |
| 11 | g of $MgSO_4 * 7 H_2O$ |
| 0.22 | g of $CaCl_2 * 2 H_2O$ | make up to 11 l with deionized water.

The mixture was sterilized at 121° C. for 30 min and then 55 ml of trace elements (2-fold concentrate) were added.

This medium was inoculated with 400 ml of preculture of *Pseudomonas burkholderia* and the fermentation was carried out in a 14 l fermenter under the following conditions for 60 h:

| | |
|---|---|
| Temperature: | 30° C. |
| Speed of rotation: | 1000 rpm |
| Gas flow rate: | 11 l/min |
| Pressure: | 0.1 bar |
| pH: | 6.5 |

The soybean oil was metered in during the fermentation, the amount metered increasing exponentially with time. After the fermentation was complete, the fermenter was cooled to 15° C. and drained.

The lipase activity of the drained crude lipase solution from *Pseudomonas burkholderi* was 8900 U/ml.

1.2 Immobilization

Before the immobilization, the crude lipase solution, drained from the fermenters, from Pseudomonas burkholderia from Example 1.1. was centrifuged in 1 l vessels in an RC-3B swing-out centrifuge at 5000–6000 rpm.

The activity of the cloudy, cell-free crude lipase solution after centrifugation of the crude lipase solution from Pseudomonas burkholderia drained from the fermenter was 10,500 U/ml.

8.3 mg of lipase are equivalent to 250,000 U

The cell-free, cloudy supernatant was incubated in various concentrations (dilution) with diverse contact times and under various conditions (pH, ionic strength) with Accurel® 1004 (polypropylene particles <400 $\mu$m) and Accurel® 1001 (polypropylene particles 400 $\mu$m to 1000 $\mu$m).

1.2.1 Immobilization on Accurel® 1004

Table 1.1 shows the dependence of the adsorption (percentage loading of the support compared with the free lipase remaining in the supernatant) and the activity of the immobilized lipase on the lipase concentration (loading) (mg of lipase/g of support)) in the crude lipase solution.

| | |
|---|---|
| Contact time: | 2 h |
| pH: | 7 |
| Ionic strength: | 3.2 mS |

TABLE 1.1

| Example | Loading [mg of lipase/g of support] | Loading of lipase on support in [%] | Activity [U/g of support] |
|---|---|---|---|
| 1.2.1 a) | 0.5 | 90 | 30 |
| 1.2.1 b) | 1 | 90 | 65 |
| 1.2.1 c) | 2.1 | 86 | 145 |
| 1.2.1 d) | 4.2 | 78 | 250 |
| 1.2.1 e) | 8.3 | 73 | 407 |

1.2.2 Immobilization on Accurel® 1001

Table 1.2 shows the dependence of the adsorption (percentage loading of the support compared with the free lipase remaining in the supernatant) and the activity of the immobilized lipase on the lipase concentration (loading) (mg of lipase/g of support)) in the crude lipase solution.

|  |  |
|---|---|
| Contact time: | 2 h |
| pH: | 7 |
| Ionic strength: | 3.2 mS |

TABLE 1.2

| Example | Loading [mg of lipase/g of support] | Loading of lipase on support in [%] | Activity [U/g of support] |
|---|---|---|---|
| 1.2.2 a) | 0.5 | 80 | 20 |
| 1.2.2 b) | 1 | 80 | 45 |
| 1.2.2 c) | 2.1 | 80 | 87 |
| 1.2.2 d) | 4.2 | 78 | 220 |
| 1.2.2 e) | 8.3 | 67 | 410 |

In all the further tests with immobilized lipase from *Pseudomonas burkholderia*, 4.2 mg of lipase/g of support were employed, and Accurel® 1001 was used as polyolefin particles.

Table 1.3 shows the dependence of the adsorption (percentage loading of the support compared with the free lipase remaining in the the supernatant) on the pH.

|  |  |
|---|---|
| Contact time: | 1 h |
| Ionic strength: | 3.2 mS |

TABLE 1.3

| Example | pH | Loading of lipase on support in [%] |
|---|---|---|
| 1.2.2 f) | 4.8 | 81 |
| 1.2.2 g) | 5.8 | 73 |
| 1.2.2 h) | 6.8 | 71 |
| 1.2.2 i) | 7.8 | 68 |
| 1.2.2 j) | 8.8 | 62 |

Table 1.4 shows the dependence of the adsorption (percentage loading of the support compared with the free lipase remaining in the supernatant) on the ionic strength (Na sulfate concentration).

|  |  |
|---|---|
| Contact time: | 1 h |
| pH: | 7 |

TABLE 1.4

| Example | Na$_2$SO$_4$ concentration in [M] | Loading of lipase on support in [%] |
|---|---|---|
| 1.2.2 k) | 0 | 68 |
| 1.2.2 l) | 0.1 | 68 |
| 1.2.2 m) | 0.5 | 50 |
| 1.2.2 n) | 1 | 50 |
| 1.2.2 o) | 2 | 31 |

Table 1.5 shows the dependence of the adsorption (percentage loading of the support compared with the free lipase remaining in the supernatant) on the contact time.

|  |  |
|---|---|
| pH: | 7 |
| Ionic strength: | 3.2 mS |

TABLE 1.5

| Example | Contact time in [h] | Loading of lipase on support in [%] |
|---|---|---|
| 1.2.2 p) | 0.16 | 60 |
| 1.2.2 q) | 0.33 | 66 |
| 1.2.2 r) | 0.66 | 64 |
| 1.2.2 s) | 1 | 68 |
| 1.2.2 t) | 1.5 | 63 |
| 1.2.2 u) | 2.0 | 63 |
| 1.2.2 v) | 4.0 | 86 |
| 1.2.2 w) | 6.0 | 91 |
| 1.2.2 x) | 8.0 | 91 |
| 1.2.2 y) | 24 | 93 |

1.2.3 Desorption of the lipase from the support material 1.2.3.1 Lipase from *Pseudomonas burkholderia*

The immobilized lipase prepared as in Example 1.2.2 d) from a crude lipase solution from *Pseudomonas burkholderia* was filtered off (filtrate of the crude lipase solution=unadsorbed constituents of the crude lipase solution), washed and contacted with a desorbing SDS buffer solution at 95° C. for 5 min. The buffer solution contains in solution the lipase which has been desorbed again and has been purified from the other constituents of the crude lipase solution.

1.2.3.1 Lipase from *Pseudomonas aeruginosa*

Immobilized lipase from *Pseudomonas aeruginosa* was prepared in analogy to Example 1.1 and Example 1.2.2 d) using *Pseudomonas aeruginosa* in place of *Pseudomonas burkholderia*.

The immobilized lipase prepared from the crude lipase solution from *Pseudomonas aeruginosa* was filtered off (filtrate of the crude lipase solution=unadsorbed constituents of the crude lipase solution), washed and contacted with a desorbing SDS buffer solution at 95° C. for 5 min. The buffer solution contains in solution the lipase which has been desorbed again and has been purified from the other constituents of the crude lipase solution.

EXAMPLE 2

Enantioselective acylation of racemic 1-phenylethanol as substrate with vinyl propionate as acylating agent in the presence of the immobilized lipase prepared in Example 1.2.2. d)

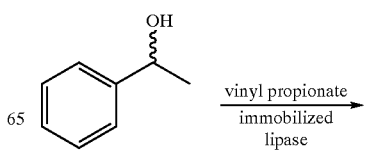

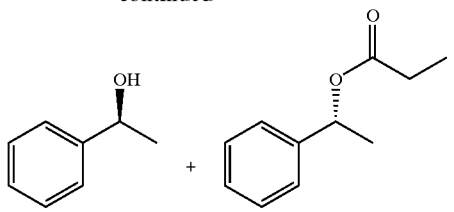

EXAMPLE 2.1

Batchwise Process

In the first place, a stock solution was prepared from 500 g (4.1 mol) of 1-phenylethanol and 246 g (2.46 mol) of vinyl propionate in 2 l of MTBE. 5 ml portions of this solution were added to an aliquot of the immobilized lipase equivalent to 10 mg of free lipase. The mixture was shaken at RT for 12 h and filtered to remove immobilized lipase, and the conversion and enantioselectivity of the acylated antipodes were determined by GC and have been listed in Table 3. The residues on the filters were washed with MTBE and employed anew in order to determine the useful life. The experimental procedure was repeated up to 10 times. The immobilized lipases used were the immobilized lipase from *Pseudomonas burkholderi* prepared in Example 1.1.2 d). The analogous experiment with the free lipase was carried out for comparison.

TABLE 3.1

Conversion (C in [%]) and enantioselectivity (ee in [%]) of the acylated antipode in the enantioselective acylation of racemic 1-phenylethanol in the presence of the free lipase in a batchwise process. The process was repeated with the lipase isolated from the preceding experiment up to 10 times.
Free lipase

| Run | C | ee |
|---|---|---|
| 1 | 50.6 | 98 |
| 2 | 44.8 | 99 |
| 3 | 42.4 | 99 |
| 4 | 38.4 | 99 |
| 5 | 23.7 | 99 |
| 10 | 11.3 | 99 |

TABLE 3.2

Conversion (C in [%]) and enantioselectivity (ee in [%]) of the acylated antipode in the enantioselective acylation of racemic 1-phenylethanol in the presence of the respective immobilized lipase in a batchwise process. The process was repeated with the immobilized lipase isolated from the preceding experiment up to 10 times.
Immobilized lipase Pseudomonas burkholderi (Ex 1.2.2 d)

| Run | C | ee |
|---|---|---|
| 1 | 50.0 | >99 |
| 2 | 49.9 | >99 |
| 3 | 49.9 | >99 |
| 4 | 49.8 | >99 |
| 5 | 49.9 | >99 |
| 10 | 49.7 | >99 |

EXAMPLE 3.2

Continuous Process

A chromatography column (1.8×15 cm) was packed with the immobilized lipase from Example 1.2.2d), and a stream of the precursor solution was pumped at 30–35 ml/h over the immobilisate. Samples were taken at regular intervals and the conversion and the enantioselectivity were determined by GC and have been listed in Table 3.4. A lyophilisate of the free lipase was employed for comparison.

TABLE 3.4

Conversion (C) and enantioselectivity (ee) in [%] measured at regular intervals during a continuous process for enantioselective acylation of racemic 1-phenylethanol. The values for the immobilized lipase from Example 1.2.2 d) are compared with the values for the free lipase.

| | Time | | | | | | | | | | | |
|---|---|---|---|---|---|---|---|---|---|---|---|---|
| | 10 h | | 20 h | | 50 h | | 100 h | | 150 h | | 200 h | |
| | C | ee | C | ee | C | ee | C | ee | C | ee | C | ee |
| Free lipase | 50.1 | 99 | 48.2 | 99 | 32.1 | 99 | 15.4 | 99 | — | | — | |
| Imm. lipase Ex.1.2.2 d) | 50.3 | 99 | 50.0 | 99 | 50.1 | 99 | 49.9 | 99 | 49.8 | 99 | 49.9 | 99 |

EXAMPLE 4

Enantioselective acylation of racemic trans-2-methoxycyclohexanol as substrate with succinic anhydride as acylating agent in the presence of the immobilized lipase prepared in Example 1.2.2 d)

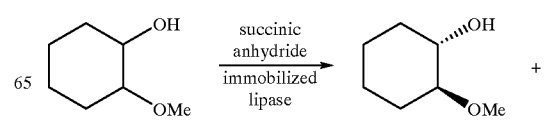

-continued

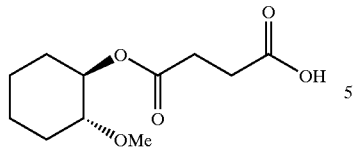

EXAMPLE 4.1

Batchwise Process

In the first place, a stock solution was prepared from 1100 g (8.46 mol) of trans-2-methoxycyclohexanol and 470 g (4.65 mol) of succinic anhydride in a mixture of 6.2 l of MTBE and 2.2 l of propylene carbonate. 5 ml portions of this solution were added to an aliquot of the immobilized lipase equivalent to 10 mg of free lipase. The mixture was shaken at RT for 12 h and filtered to remove immobilized lipase, and the conversion and enantioselectivity of the unacylated antipodes were determined by GC and have been listed in Table 4. The residues on the filters were washed with MTBE and employed anew in order to determine the useful life. The experimental procedure was repeated up to 10 times. The immobilized lipases used were the lipases prepared in Example 1.1.2 d). The analogous experiment with the free lipase was carried out for comparison.

TABLE 4.1

Conversion (C in [%]) and enantioselectivity (ee in [%]) of the unacylated antipode in the enantioselective acylation of racemic trans-2-methoxycyclohexanol in the presence of the free lipase in a batchwise process. The process was repeated with the lipase isolated from the preceding experiment up to 10 times.
Free lipase

| Run | C | ee |
|---|---|---|
| 1 | 54.5 | 99 |
| 2 | 47.3 | 88 |
| 3 | 43.2 | 75 |

TABLE 4.1-continued

Conversion (C in [%]) and enantioselectivity (ee in [%]) of the unacylated antipode in the enantioselective acylation of racemic trans-2-methoxycyclohexanol in the presence of the free lipase in a batchwise process. The process was repeated with the lipase isolated from the preceding experiment up to 10 times.
Free lipase

| Run | C | ee |
|---|---|---|
| 4 | 29.4 | — |
| 5 | 14.5 | — |
| 10 | 3.4 | — |

TABLE 4.2

Conversion (C in [%]) and enantioselectivity (ee in [%]). of the unacylated antipode in the enantioselective acylation of racemic trans-2-methoxycyclohexanol in the presence of the respective immobilized lipase in a batchwise process. The process was repeated with the immobilized lipase isolated from the preceding experiment up to 10 times.
Immobilized lipase Pseudomonas burkholderi (Ex. 1.2.2 d))

| Run | C | ee |
|---|---|---|
| 1 | 55.0 | >99 |
| 2 | 54.5 | >99 |
| 3 | 53.8 | >99 |
| 4 | 54.2 | >99 |
| 5 | 54.6 | >99 |
| 10 | 54.6 | >99 |

EXAMPLE 4.2

Continuous Process

A chromatography column with a diameter of 1 cm was packed with the immobilized lipase from Example 1.2.2. f), and a stream of the precursor solution was pumped at 30–35 ml/h over the immobilisate. Samples were taken at regular intervals and the conversion and the enantioselectivity were determined by GC and have been listed in Table 4.3. A lyophilisate of the free lipase was employed for comparison.

TABLE 4.3

Conversion (C) and enantioselectivity (ee) in [%] measured at regular intervals during a continuous process for enantioselective acylation of racemic trans-2-methoxycyclohexanol. The values for the immobilized lipase from Example 1.2.2 f) are compared with the values for the free lipase.

| | Time | | | | | | | | | | |
|---|---|---|---|---|---|---|---|---|---|---|---|
| | 10 h | | 20 h | | 50 h | | 100 h | | 150 h | | 200 h | |
| | C | ee | C | ee | C | ee | C | ee | C | ee | C | ee |
| Free lipase | 54.9 | 99 | 42.3 | 69 | 28.2 | 28 | 19.4 | — | — | — | — | — |
| Imm. lipase Ex.1.2.2 f) | 55.0 | 99 | 53.8 | 99 | 54.6 | 99 | 54.0 | 99 | 54.2 | 99 | 53.9 | 99 |

We claim:

1. A process for preparing immobilized lipase consisting essentially of contacting a crude lipase solution with non-polar polyolefin particles to absorb lipase in the solution to the particles, wherein said crude lipase solution contains more than 2% by weight of impurities comprising proteins other than lipase, cellular constituents of a lipase-producing microorganism and or nutrient media residues.

2. The process as claimed in claim 1, wherein the crude lipase solution is a cell-free culture broth which is obtained by
   a) cultivating a lipase-producing organism, and
   b) then removing cells of said lipase-producing organism.

3. A process as claimed in claim 1, wherein the lipase used is the lipase from *Pseudomonas burkholderia* or *Pseudomonas aeruginosa*.

4. An immobilized lipase obtained by a process as claimed in claim 1.

5. A process for the enzyme-catalyzed conversion or enantioselective conversion of substrates, which comprises reacting the substrates in contact with the immobilized lipase as claimed in claim 4.

6. A process as claimed in claim 5, wherein the substrates used are alcohols, amines or amino esters, and these are acylated or enantioselectively acylated in the presence of an acylating agent.

7. A process as claimed in claim 5, wherein the substrates used are carboxylic esters, and these are hydrolyzed or enantioselectively hydrolyzed.

8. A process for preparing optically active compounds, which comprises enantioselectively reacting mixtures of stereoisomers or racemates of substrates in contact with the immobilized lipase as claimed in claim 4, and then fractionating the mixtures.

9. A process as claimed in claim 8, wherein the substrates used are alcohols, amines or amino esters, and these are enantioselectively acylated in the presence of an acylating agent.

10. A process as claimed in claim 8, wherein the substrates used are carboxylic esters, and these are enantioselectively hydrolyzed.

* * * * *

UNITED STATES PATENT AND TRADEMARK OFFICE
CERTIFICATE OF CORRECTION

PATENT NO. : 6,596,520 B1
DATED : July 22, 2003
INVENTOR(S) : Friedrich et al.

It is certified that error appears in the above-identified patent and that said Letters Patent is hereby corrected as shown below:

Column 17,
Line 4, "absorb" should be -- adsorb --;
Line 8, "and or" should be -- and/or --.

Signed and Sealed this

Ninth Day of September, 2003

JAMES E. ROGAN
*Director of the United States Patent and Trademark Office*